United States Patent [19]

McKibben et al.

[11] Patent Number: 5,290,556
[45] Date of Patent: Mar. 1, 1994

[54] PLASTIC BAIT COMPOSITION FOR ATTRACTING AND KILLING CROP PESTS

[75] Inventors: Gerald H. McKibben; Joseph C. Dickens; James W. Smith, all of Starkville, Miss.

[73] Assignee: The United States of America as represented by the Secretary of Agriculture, Washington, D.C.

[21] Appl. No.: 473,757

[22] Filed: Feb. 2, 1990

[51] Int. Cl.$^5$ .................. A01N 25/08; A01N 25/28
[52] U.S. Cl. .................. 424/405; 424/408; 424/409; 424/410
[58] Field of Search ............. 424/405, 408, 409, 410

[56] References Cited

U.S. PATENT DOCUMENTS

| | | | |
|---|---|---|---|
| 3,318,769 | 5/1967 | Folekemer et al. | 514/144 |
| 3,803,303 | 4/1974 | McKibben et al. | 424/84 |
| 4,027,420 | 6/1977 | McKibben et al. | 43/124 |
| 4,237,113 | 12/1980 | Cardarelli | 514/86 |
| 4,369,176 | 1/1983 | Ott | 424/84 |
| 4,808,615 | 2/1989 | Ott et al. | 514/89 |
| 4,818,525 | 4/1989 | Kamada et al. | 514/464 |
| 4,851,218 | 7/1989 | Hildebrandt et al. | 424/84 |
| 4,889,710 | 12/1989 | Hagarty | 424/45 |
| 4,965,287 | 10/1990 | Stendel et al. | 514/531 |

OTHER PUBLICATIONS

McKibben, Thompson, Parrott, Thompson and Lusby, Identification of Feeding Stimulants for Boll Weevils From Cotton Buds and Anthers, Jan. 9, 1985.
Hunter and Hinds, 1905, "The Mexican Cotton Boll Weevil", USDA Bur. Entomol. Bull 51, 181 pages.
Daum et al, 1967, "Development of the bait principle . . ." J. Econ. Entomol. 60:321–325.
McLaughlin, 1967, J. Invert. Path. 9:70–77.
Lloyd et al, 1968, J. Econ. Entomol., 61:1440–1444.
Tumlinson et al, 1969, Science 166:1010–1012.
McKibben and Davich, 1975, Ms. Ag. and Forestry Exp. Station Res. Report 1, 4 pages.
McKibben, et al., J. Chem. Ecol., vol. 11, No. 9, (1985), pp. 1229–1238.
Warnaar, F., Phytochemistry, vol. 20, (1981), pp. 89–91.

Primary Examiner—Thurman K. Page
Assistant Examiner—Robert H. Harrison
Attorney, Agent, or Firm—M. Howard Silverstein; John F. Fado

[57] ABSTRACT

This invention is directed to insect control using compositions having attractants, feeding stimulants and toxicants compounded into plastic bait pellets. These pellets are easily handled for distribution in the field. Insects are attracted to the bait pellets, induced to feed and subsequently die. The pellets have the unique advantage of being relatively impervious to environmental conditions and non-polluting.

7 Claims, 1 Drawing Sheet

PLASTIC BAIT COMPOSITION FOR ATTRACTING AND KILLING CROP PESTS

BACKGROUND OF THE INVENTION

1. Field of the Invention

This invention relates to control of insects, particularly to the killing of coleopterous chewing pests using insecticide compositions comprising an attractant and a toxicant. Additionally, the invention relates to a process for the manufacture of the compositions using plastisol material.

2. Description of the Prior Art

Boll weevils, *Anthonomus grandis* Boheman (Coleoptera: Curculionidae), are insect pests that feed on cotton plants causing serious damage to the plants and reducing harvest yield. Previous attempts have been made to trap, kill or destroy the boll weevil, for example, male sex pheromone Grandlure baited traps have been used to capture the weevils that were attracted to it. Compositions alone or in combination with traps have incorporated the use of feeding stimulants to induce the insects to feed on a toxic bait. Traps were also made of paper or plastic in the form of a container attached to the top of a cone capturing weevils alive. U.S. Pat. No. 3,803,303 describes boll weevil attractant compositions using Grandlure. Additionally, U.S. Pat. No. 4,027,420 describes an apparatus and method for attracting and killing boll weevils in which a solid support is used to contain and attractant as well as a toxicant.

U.S. Pat. No. 3,803,303 describes polymeric compositions for attracting boll weevils using a sex attractant in combination with polyethylene glycol and a toxicant such as p-dichlorobenzene. Additionally the plant attractants, caryophylline oxide and beta-bisabalol were used. In each case the attractant was applied to cotton dental-rolls.

U.S. Pat. No. 4,027,420 describes an apparatus and method for attracting and killing boll weevils. The apparatus consists of two pieces of posterboard connected together. The posterboard is impregnated with an attractant and a toxicant.

There are many disadvantages in using presently available insecticides. Toxicity to humans and animals is high. Additionally, many of the compounds are not readily degradable and thus tend toward environmental pollution. It can be seen there is a pressing need to provide a means for reducing or eliminating the amount of toxic insecticides used in the management of insect pests.

The prior art uses of toxic baits have been in various water-based forms. These bait formulations have been subject to dissolution, dilution, or wash-off by rain. More specifically, there is a need for a means to kill chewing insect pests that does not suffer the disadvantages of the prior art insecticide traps or baits described above and that is species specific thus protecting the insect species that are beneficial to crop plants.

SUMMARY OF THE INVENTION

This invention relates to compositions, apparatus and methods for attracting and killing or destroying chewing pests such as armyworm, boll weevil, boll worm, loopers, cutworms and the larvae & adults of many other leptodopterous and coleopterous pests. Surprisingly, it was found that insects can be encouraged to feed on a polymer based insecticide composition impervious to environmental conditions. The composition comprises:

a) a polymer,
b) synthetic or natural pheromones,
c) one or more feeding stimulants, and
d) a toxicant or a biological control agent.

Various forms of the invention are described, including solid pellets and hollow tubes that can be filled with any bait mixture. In one form of the invention, a plastisol is prepared from PVC powder with crude cottonseed oil as the plasticizer. Pellets are prepared by dip molding. The cottonseed oil contains both attractants and feeding stimulants for boll weevils and also functions uniquely as an integral part of the PVC matrix.

In the dip molding process, the dip molds are heated to a temperature sufficient to provide full curing of the PVC forming the inner core, typically 170°–180° C., to provide a durable support structure and to provide for a controlled release of pheromone. After dipping, the resulting tubular structure is cured in an oven at a temperature just high enough to achieve a solid, non-tacky surface but low enough to provide a friable surface that insects can chew and ingest.

Alternative designs include microspheres or solid cast pellets that are used in a manner similar to the hollow tubes. One advantage in a solid pellet is that mass production is possible by extruding and cutting to the desired length. Another design is to fill the hollow tube with a liquid or gelled bait mixture. This has the advantage that a heat-sensitive material can be used that would be destroyed or driven off by the heat treatment used to cure the PVC. An example of such a material is a biological control agent such as *Bacillus thuringiensis* spores. A biological control agent has the advantage of being environmentally more acceptable than a chemical insecticide.

Laboratory bioassays have shown that boll weevils are attracted to and induced to eat bait pellets prepared in the foregoing manner. A toxicant has been incorporated into the plastisol which kills the boll weevils that ingest it.

The pellets when applied in the field attract and induce insects to ingest particles of the pellets. Subsequently, the insects die or are rendered infertile depending on the choice of toxicant. The invention as described has the advantages of minimizing the amount of toxic substances released into the environment, being species specific and eliminating the need for constant pesticide reapplication.

DESCRIPTION OF THE PREFERRED EMBODIMENTS

EXAMPLE 1

Figure 1:
FIG. 1 is a photograph that shows boll weevils attracted to and feeding on plastic bait pellets.

The following components were mixed together by weight to form a plastisol:

| | |
|---|---|
| Polyvinyl chloride (PVC) | 53.29% |
| Dioctylphthalate (DOP) | 35.60% |
| Lauric acid ester of phytol (feeding stimulant) | 4.50% |
| Grandlure (sex pheromone) | 0.214% |
| Titanium dioxide (pigment) | 5.40% |
| Propoxur | 1.00% |

Pellets of the above plastisol material were prepared using a dip moulding process in which steel rods were heated to about 182 degrees centigrade. The rods were dipped into the plastisol for about 25 seconds then withdrawn. The rods were then cured by allowing to stand for 30 more seconds either alone at ambient temperature or in a oven heated to about 170 to 190 degrees centigrade. The pellets were then removed. By increasing the PVC ratio of the above composition a tougher, more durable pellet can be obtained. Additionally, other phthalates can be used as functional equivalents. Although cottonseed oil will work alone as the plasticizer, ratios of DOP and cottonseed oil can be adjusted for optimum feeding stimulancy/durability properties. The ester feeding stimulant can be added at a concentration of from 0.001% by weight to 25% by weight. Grandlure (the synthetic pheromone) can be added at a concentration of from $1\times10^{-8}\%$ to $5\times10^{-4}\%$ by weight.

The pigment in the composition of the preferred embodiment can be eliminated and still elicit the desired effects; however, additions of a pigment is advantageous for at least two reasons:

(1) fundamentally the pigment serves as an ultra-violet light (UV) protectant for the PVC, thus retarding breakdown of the polymer; and (2) addition of pigment serves as a color attractant enhancing the ability of the composition to attract insects.

It is envisioned that any of the conventional plastics can be used alternatively in the present invention and are listed in Table 1.

TABLE 1

| Alternative Polymers | |
|---|---|
| Acrylic | Chlorinated diphenyl |
| Alkyd | Chlorinated rubber |
| Ally | Copal ester |
| Aniline-formaldehyde | Coumarone-Indene |
| Aramid | Cyclohexanone-formaldehyde |
| Bituminous | Epoxy, epichrorhydrin-bisphenol |
| Caffelite | Ethyl cellulose |
| Casein | Formaldehyde-sulfonanide |
| Cellulose | Furane |
| Cellulose acetate | Fluorocarbons |
| Cellulose acetate-butyrate | Hydrogenated rosins |
| Cellulose acetate-propionate | Lignins |
| Cellulose propionate | Melamine |
| Methylcellulose | Urethanes |
| Phenol-aldehyde | Vinyl polymers, i.e. |
| Phenol-copal | Polyvinyl acetate (PVAC) |
| Polycarbonates | PVAC, vinylidene dinitrile |
| Polyamides | Polyvinyl alcohol (PVAL) |
| Polyamide-aldehyde | Polyvinyl aldehyde |
| Polyesters | Polyvinyl chloride (PVC) |
| Polyethylenes | PVC and acetate |
| Polystyrenes | Polyvinylidene |
| Rubber hydrochloride | |
| Silicones | |
| Sulfonamide-aldehyde | |
| Urea- (form)aldehyde | |

The feeding stimulant can alternately be left out of the plastisol composition. After the dip moulding process resulting in a hollow pellet, the feeding stimulant can be put inside the hollow laced pellet.

In the context of the present invention, the term toxicant is understood to means substances that are used in the management, inhibition or killing of crop pests, the choice of which is within the purview of the skilled artisan. Additionally, the term toxicant is meant to include microorganisms effective as biocontrol agents. These agents, adversely affected by the heating of the dip moulding process, can be placed in the hollow of the resulting pellets thereby maintaining their viability.

EXAMPLE 2

The pellets obtained from EXAMPLE 1 were used in a laboratory feeding stimulant bioassay in which it was shown that the pellets attracted boll weevils and induced the insects to feed on the bait pellets. Insects induced to feed were killed. Additionally, the pellets of the above preparation killed boll weevils that remained in contact with the pellets for about 5 minutes regardless of whether they fed or not.

Bioassay Protocol

Laboratory reared boll weevils, 1 to 4 weeks old, were used in the bioassays. For bioassay of the plastic bait compositions, pellets were prepared as above. The pellets were then placed into cages containing boll weevils, and the cages placed in a dark environment overnight at 29° C. Feeding response was determined by totaling the number of feeding punctures within the bait pellets. Results indicate that the plastic bait pellets are extremely effective at both attracting as well as inducing the insects to feed, (see FIG. 1).

Control pellets which did not contain either the sex pheromone attractant or the feeding stimulant did not elicit an attraction or feeding response.

Field Study

The plastic bait pellets were tested in the field for efficacious attractant activity using kill pans having an alcoholic solution therein. These pans serve as a means for collecting and preserving the killed insects during the experiments. A wooden stake was driven through the center of the kill pan into the ground. Bundt or angel food cake pans having a hollow center serve ideally as kill pans. Bait pellets were placed on top of the stake. Kill pans were also placed in the field having pellets made containing no attractants thereby serving as control.

The kill pans were allowed to stay in the field for up to three weeks after which the number of weevils in the kill pans were enumerated. The number of weevils found in the kill pans were as high as 481/pan during the three week period. We have found that pellets without the attractant-feeding stimulant do not attract the insects. The results clearly indicate the bait pellets of the instant invention are effective at attracting large numbers of insects.

Another field test was set up in Clay County, Miss. with six of the devices as described, with aluminum pans below the stakes to facilitate counting of dead boll weevils. After 12 days, the six pans had a total of 950 dead boll weevils.

Similarly, a test was set up at another location in Clay County, Miss. with 11 bait devices, also fitted with aluminum pans. Counts of dead boll weevils are shown in Table 2.

TABLE 2

| | No. dead weevils on indicated day | | |
|---|---|---|---|
| Station no. | Day 1 | Day 2 | Day 3 |
| 1 | 53 | 58 | 43 |
| 2 | 69 | 30 | 25 |
| 3 | 31 | 28 | 35 |
| 4 | 44 | 16 | 31 |
| 5 | 46 | 22 | 10 |
| 6 | 35 | 31 | 14 |
| 7 | 35 | 52 | 15 |

TABLE 2-continued

| Station no. | No. dead weevils on indicated day | | |
| --- | --- | --- | --- |
| | Day 1 | Day 2 | Day 3 |
| 8 | 35 | 37 | 21 |
| 9 | 49 | 49 | 37 |
| 10 | 43 | 55 | 24 |
| 11 | 30 | 28 | 17 |
| TOTALS | 470 | 406 | 272 |

Observation revealed that only about one-half the weevils that were affected by the toxicant actually fell into the pans. About two dozen weevils that came into contact with the bait and left before being affected were captured and taken into the laboratory for observation. All died within 12 hours, while a similar group of weevils that had not come in contact with the bait were all alive in the same length of time. Thus the actual number of weevils killed by the bait is approximately double the pan totals shown previously.

There has been provided in accordance with the present invention, compositions, articles of manufacture and the use thereof for the advantages described herein above in the management of coleopterous insect pests.

The invention as described by the specific embodiments is not meant to limit its scope. It is envisioned and apparent that many alternatives and variations may be encompassed by the present invention. It is intended that the spirit and scope of this disclosure include such alternatives and variations.

We claim:

1. A plastisol composition comprising:
   a) a polymer
   b) one or more synthetic or natural insect pheromones
   c) one or more insect feeding stimulants, and
   d) an insect toxicant.

2. The plastisol composition of claim 1, wherein the composition additionally comprises:
   a) a pigment.

3. The plastic bait insecticide composition of claim 1, wherein the polymer is polyvinyl chloride.

4. A method for controlling insect pests comprising:
   a) administering to a predetermined site an effective insect controlling amount of a bait composition comprising the composition of claim 1.

5. A method for the preparation of a plastic bait insecticide comprising:
   a) forming a plastisol mixture comprising:
      i) a polymer
      ii) one or more synthetic or natural insect pheromones
      iii) one or more insect feeding stimulants, and
      iv) an insect toxicant; and
   b) curing said mixture to form a plastic.

6. An article of manufacture consisting essentially of
   a) a solid polymer container having therein a plastisol composition comprising:
      i) one or more synthetic or natural insect pheromones
      ii) one or more insect feeding stimulants, and
      iii) an insect toxicant.

7. The article of manufacture of claim 6 wherein said container is selected from the group consisting of tubes and microspheres.

* * * * *